(12) United States Patent
Bennett et al.

(10) Patent No.: US 6,187,585 B1
(45) Date of Patent: *Feb. 13, 2001

(54) OLIGONUCLEOTIDE INHIBITION OF EPIDERMAL GROWTH FACTOR RECEPTOR EXPRESSION

(75) Inventors: C. Frank Bennett, Carlsbad, CA (US); Allan Lipton, Hershey; Lois M. Witters, York Haven, both of PA (US)

(73) Assignees: Isis Pharmaceuticals, Inc., Carlsbad, CA (US); The Penn State Research Foundation, University Park, PA (US)

( * ) Notice: Under 35 U.S.C. 154(b), the term of this patent shall be extended for 0 days.

This patent is subject to a terminal disclaimer.

(21) Appl. No.: 09/306,876

(22) Filed: May 7, 1999

Related U.S. Application Data

(63) Continuation of application No. 08/832,658, filed on Apr. 4, 1997, now Pat. No. 5,914,269.

(51) Int. Cl.[7] .......................... C07H 21/04; A61K 48/00; C12Q 1/68
(52) U.S. Cl. ..................... 435/375; 435/6; 536/23.1; 536/24.1; 536/24.5; 514/44
(58) Field of Search .................. 435/6, 375; 514/44; 536/23.1, 24.1, 24.5

(56) References Cited

U.S. PATENT DOCUMENTS

| | | | |
|---|---|---|---|
| 5,225,326 | 7/1993 | Bresser et al. | 435/6 |
| 5,585,479 | 12/1996 | Hoke et al. | 536/24.5 |
| 5,610,288 | 3/1997 | Rubenstein | 536/24.5 |

FOREIGN PATENT DOCUMENTS

WO 96/16988    6/1996  (WO) .

OTHER PUBLICATIONS

Agrawal, S., "Antisense Oligonucleotides: Towards Clinical Trials," *Tibtech*, Oct. 1996, 14, 376–387.
Branch, A.D. et al., "A Good Antisense Molecule is Hard to Find," *TIBS*, Feb. 1998, 23, 45–50.
Chakrabarty et al., "Expression of antisense epidermal growth factor receptor RNA downmodulates the malignant behavior of human colon cancer cells", *Clin. Exp. Metastasis*, 1995, 13, 191–195.
Coulson et al., "A Nonantisense Sequence–Selective Effect of a Phosphorothioate Oligodeoxynucleotide Directed against the Epidermal Growth Factor Receptor in A431 Cells", *Molecular Pharmacology*, 1996, 50, 314–325.
De Giovanni et al., "Antisense Epidermal Growth Factor Receptor Trasfection Impairs the Proliferative Ability of Human Rhabdomyosarcoma Cells", *Cancer Res.*, 1996, 56, 3898–3901.
Hall et al., "Models of Pancreatic Cancer", *Cancer Surveys: The Molecular Pathology of Cancer*, 1993, 16, 135–155.
Kunkel et al., "Inhibition of the epidermal growth factor receptor tyrosine kinase by PD153035 in human A431 tumors in athymic nude mice", *Invest. New Drugs*, 1996, 13, 295–302.

Moroni et al., "EGF–R Antisense RNA Blocks Expression of the Epidermal Growth Factor Receptor and Suppresses the Transforming Phenotype of a Human Carcinoma Cell Line", *J. Biol. Chem.*, 1992, 267(5), 2714–2722.
Rajagopal et al., "Epidermal Growth Factor Expression in Human Colon and Colon Carcinomas: Anti–Sense Epidermal Growth Factor Receptor RNA Down–Regulates the Proliferation of Human Colon Cancer Cells", *Int. J. Cancer*, 1995, 62, 661–667.
Rubenstein et al., "Antisense Oligonucleotide Intralesional Therapy for Human PC–3 Prostate Tumors Carried in Athymic Nude Mice", *J. Surgical Oncology*, 1996, 62, 194–200.
Sanghvi et al., "Antisense oligodeoxynucleotides: synthesis, biophysical and biological evaluation of oligodeoxynucleotides containing modified pyrimidines", *Nucl. Acids Res.*, 1993, 21(14), 3197–3203.
Sanghvi, *Antisense Research and Application*, S.T. Crooke and B. Lebleu (eds.), CRC Press, Chapter 15, 1993, 273–288.
Tonghua et al., "Effects of Antisense Epidermal Growth Factor and its Receptor Retroviral Expression Vectors on Cell Growth of Human Pancreatic Carcinoma Cell Line", *Chinese Med. J.*, 1995, 108(9), 653–659.
Stull, R.A. et al., "Antigene, Ribozyme and Aptamer Nucleic Acid Drugs: Progress and Prospects", *Pharamac. Res*, 1995, 12, 465–483.
Wang et al., "Delivery of antisense oligodeoxyribonucleotides against the human epidermal growth factor receptor into cultured KB cells with liposomes conjugated to folate via polyethylene glycol", *Proc. Natl. Acad. Sci. USA*, 1995, 92, 3318–3322.
Yoneda et al., "The Antiproliferative Effects of Tyrosine Kinase Inhibitors Tyrphostins on a Human Squamous Cell Carcinoma in Vitro and in Nude Mice", *Cancer Res.*, 1991, 51, 4430–4435.
Kraus et al., "Isolation and characterization of ERBB3, a third member of the ERBB/epidermal growth factor receptor family: Evidence for overexpression in a subset of human mammary tumors," *Proc. Natl. Acad. Sci. USA*, 1989, 86, 9193–9197.
Normanno et al., "Growth Inhibition of Human Colon Carcinoma Cells by Combinations of Anti–Epidermal Growth Factor–related Growth Factor Antisense Oligonucleotides," *Clin. Cancer Res.*, 1996, 2, 601–609.
Ullrich et al., "Human epidermal growth factor receptor cDNA sequence and aberrant expression of the amplified gene in A431 epidermoid carcinoma cells," *Nature*, 1984, 309, 418–425.

*Primary Examiner*—Robert A. Schwartzman
*Assistant Examiner*—Sean McGarry
(74) *Attorney, Agent, or Firm*—Woodcock Washburn Kurtz Mackiewicz & Norris LLP

(57) ABSTRACT

Compounds, compositions and methods are provided for inhibiting the expression of human EGFR. The compositions comprise oligonucleotides complementary to mRNA targeted to nucleic acids encoding EGFR. Methods of using these oligonucleotides for inhibition of EGFR expression and for treatment of diseases such as cancers associated with overexpression of EGFR are provided.

23 Claims, No Drawings

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 1
gaggcgttct cctttctcca                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Combined DNA/RNA Molecule:
      Oligonucleotide
<223> OTHER INFORMATION: Description of Artificial Sequence: Novel
      Sequence

<400> SEQUENCE: 2
gaggcgttct cctuucucca                                              20

```
<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 3
tgtcggcccc acaggctcgg                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 4
cgcccggagc actgctgggc                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 5
ccccagcagc tcccattggg                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Combined DNA/RNA Molecule:
      Oligonucleotide
<223> OTHER INFORMATION: Description of Artificial Sequence: Novel
      Sequence

<400> SEQUENCE: 6
ccccagcagc tcccauuggg                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 7
ccacgttgca cagggcaggg                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 8
ctcggctgac attccggcaa                                              20
```

```
<210> SEQ ID NO 9
<211> LENGTH: 20
<212> TYPE: DNA
<213> ORGANISM: Artificial Sequence
<220> FEATURE:
<223> OTHER INFORMATION: Description of Combined DNA/RNA Molecule:
      Oligonucleotide
<223> OTHER INFORMATION: Description of Artificial Sequence:  Novel
      Sequence

<400> SEQUENCE: 9
cucggctgac attccggcaa                                                    20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:  Novel
      Sequence

<400> SEQUENCE: 10
gagttcgcgt cctttctcca                                                    20
```

OLIGONUCLEOTIDE INHIBITION OF EPIDERMAL GROWTH FACTOR RECEPTOR EXPRESSION

This Application is a continuation of U.S. provisional Application Ser. No. 08/832,658 filed Apr. 4, 1997 and now U.S. Pat. No. 5,914,269.

FIELD OF THE INVENTION

The present invention provides compositions and methods of modulating the expression of epidermal growth factor receptor. Many human tumors have been found to overexpress this receptor and such enhanced expression has been shown to be correlated with poor prognosis. In particular, this invention relates to oligonucleotides specifically hybridizable with nucleic acids encoding human EGFR. These oligonucleotides have been found to inhibit the expression of EGFR.

BACKGROUND OF THE INVENTION

Epidermal Growth Factor Receptor (EGFR) is a specific receptor for epidermal growth factor (EGF) and transforming growth factor-α (TGF-α). When these mitogenic polypeptides bind to EGFR, tyrosine kinase activity of the receptor is induced, and this in turn triggers a series of events which regulate cell growth. A number of malignant and non-malignant disease conditions are now believed to be associated with EGFR, particularly aberrant expression of EGFR. Aberrant expression includes both increased expression of normal EGFR and expression of mutant EGFR. Overexpression of EGFR is found in many human tumors including most glioblastomas and breast, lung, ovarian, colorectal, bladder, pancreatic, squamous cell and renal carcinomas. Elevated EGFR levels correlate with poor prognosis in human tumors. EGFR is also implicated in nonmalignant diseases, such as psoriasis. The sequence of the mRNA encoding human EGFR is known. Ullrich et al., *Nature*, 1984, 309, 418; GenBank Accession Number X00588. The gene encoding EGFR is also known as c-erb-B1. Two EGFR transcripts typically appear on Northern blots, one measuring 10 kb and one measuring 5.6 kb.

A number of inhibitors of EGFR have been shown to be effective in inhibiting the growth of human tumor cells. Monoclonal antibodies to EGFR and drugs which inhibit EGFR tyrosine kinase activity can inhibit the growth of human cancer cell xenografts in nude mice. Normanno et al., *Clin. Cancer Res.*, 1996, 2, 601. The drug PD153035, which inhibits EGFR tyrosine kinase activity, can inhibit the growth of A431 cells in nude mice, and tyrphostins, which inhibit the activity of EGFR as well as other tyrosine kinases, have been shown to inhibit the growth of squamous carcinoma in nude mice. Kunkel et al., *Invest. New Drugs*, 1996, 13, 295 and Yoneda et al., *Cancer Res.*, 1991, 51, 4430.

Vectors expressing EGFR nucleic acid sequences in an orientation complementary to mRNA have been used to study the effects of EGFR on proliferation of cultured cancer cells. Transfectants of the human epidermoid carcinoma KB cell line expressing EGFR cDNA or RNA sequences in an orientation complementary to mRNA exhibited restored serum-dependent growth and impaired colony formation and growth in agar. Moroni et al., *J. Biol. Chem.*, 1992, 267, 2714. Human pancreatic carcinoma cells of the PC-7 cell line transfected with vectors expressing EGFR cDNA sequences in an orientation complimentary to mRNA showed inhibited cell growth, colony formation and tumorigenicity in nude mice. Liu et al., *Chinese Medical Journal*, 1995, 108, 653. Transfection of human colon cancer cell lines with EGFR RNA expression vectors producing an oligonucleotide complementary to mRNA caused a reduction in cell proliferation and ability to grow on soft agar. Rajagopal et al., *Int. J. Cancer*, 1995, 62, 661. Human rhabdomyosarcoma cells transfected with a plasmid expressing EGFR cDNA in an orientation complementary to mRNA had greatly impaired proliferation. De Giovanni et al., *Cancer Res.*, 1996, 56, 3898.

Considerable research is being directed to the application of oligonucleotides complementary to MRNA and other oligomers for therapeutic purposes. Oligonucleotides complementary to MRNA have already been employed as therapeutic moieties in the treatment of disease states in animals and man, and compositions comprising oligomers complementary to mRNA have been shown to be capable of modulating expression of genes implicated in viral, fungal and metabolic diseases. Further, oligonucleotides complementary to mRNA have been safely administered to humans and clinical trials of approximately a dozen oligonucleotide drugs targeted to viral and cellular gene products are underway.

Oligodeoxyribonucleotides complementary to mRNA targeted to EGFR have been encapsulated into liposomes linked to folate via a polyethylene glycol linker and delivered into cultured human epidermoid carcinoma KB cells. The oligonucleotides were a phosphodiester (P=O) 15-mer complementary to the EGFR gene stop codon, or the same sequence with three phosphorothioate (P=S) linkages at each end. Both of these oligonucleotides reduced KB cell proliferation by greater than 90% after treatment with 3 μM oligonucleotide in folate-PEG-liposomes. In contrast, free P=O oligonucleotide caused almost no growth inhibition, and free P=S-capped oligonucleotide caused only a 15% growth inhibition, even at this high dosage level. EGFR expression, measured by indirect immunofluorescence, was virtually abolished in cells treated with either of the folate PEG-liposome-encapsulated oligonucleotides but EGFR expression was qualitatively similar to untreated cells after treatment with free oligonucleotide. Wang et al., *Proc. Natl. Acad. Sci. USA*, 1995, 92, 3318.

A 15-mer phosphorothioate oligonucleotide complementary to the translation initiation region of EGFR mRNA was found to inhibit cell proliferation by over 25% in A431 cells, derived from a vulval carcinoma. This activity, though dose-dependent from 1–25 μM, was not mediated by an antisense mechanism, as demonstrated by a lack of reduction in either EGFR protein or mRNA after oligonucleotide treatment. In addition, an 18-mer oligonucleotide complementary to mRNA targeted to the same region had no effect even at the highest (25 μM) dose, and neither oligonucleotide had any effect in the two other tumor-derived cell lines tested. Coulson et al., *Mol. Pharm.*, 1996, 50, 314.

The suppression of growth of pancreatic carcinoma cell lines by undisclosed oligonucleotides complementary to mRNA inhibiting the expression of TGF-α and/or the EGFR has been reported. Hall et al., unpublished data, reported in Hall and Lemoine, Models of Pancreatic Cancer, in *Cancer Surveys*, Volume 16: *The Molecular Pathology of Cancer*, 1993, p.135–155.

Rubenstein et al. have reported treatment of established human-derived prostate tumor xenografts in nude mice by intralesional injection of oligonucleotides complementary to mRNA directed against mRNAs encoding TGF-α and EGFR. The oligonucleotides included 39-mers complementary to 18 bases located 5' and 3' from the AUG mRNA translation initiation codon of either TGF-α or EGFR sequence. The oligonucleotides were phosphorothioated at each of three terminal bases at both the 5' and 3' ends. The oligonucleotides were administered either alone or in combination, with the combination treatment proving most effective. *J. Surg. Oncol.*, 1996, 62, 194. In U.S. Pat. No. 5,610,288, Rubenstein et al. disclose polynucleotides of about 20 to 50 nucleic acid bases, most preferably about 40 nucleic acid bases in length, which preferentially hybridize to the start codon of the mRNA encoding EGFR. A preferred embodiment is a 39-mer including 18 bases complementary to the 5' side of the translation initiation codon. This oligonucleotide inhibited PC-3 cell growth when administered in combination with an oligonucleotide complementary to mRNA targeted to TGF-α. Alone, the EGFR oligonucleotide gave inhibition of cell growth equivalent to that achieved with an inverted (5' to 3') version of the same sequence.

Rearrangements or deletions of the EGFR gene resulting in mutant EGFR protein have been found in some cancers. The in-frame deletion from nucleotides 275–1075 in the EGFR has been referred to as class I, Type I or Type III mutation. WO 96/16988 (Wong et al.) discloses cell lines capable of overexpressing Type III mutant EGFR, vaccines for inhibiting tumor formation comprising peptides similar to a fusion junction present in mutant human EGFR, antibodies raised against a cell line overexpressing Type III mutant EGFR, and oligonucleotides complementary to mRNA targeted to a Type III mutant EGFR which decrease expression of a mutant EGFR. In a preferred embodiment, the oligonucleotide complementary to mRNA contains sequences from what were formerly distant portions of the normal EGFR cDNA. The oligonucleotide must contain the sequence 5'-TACCTT-3'. An 18-mer oligonucleotide containing this sequence was found to downregulate mutant EGFR levels when given at a 40 μM dose in cultured cells which overexpressed Type III mutant EGFR.

The present invention provides new oligonucleotide compounds complementary to mRNA, as well as other oligonucleotide compounds, and compositions comprising the same together with methodologies for the use of certain compounds of the invention for interfering with translation of selected mRNA targets related to epidermal growth factor receptor.

SUMMARY OF THE INVENTION

The present invention is directed to oligonucleotides, especially those from 12–25 nucleotides in length, which are complementary to a nucleic acid molecule encoding EGFR, and which inhibit the expression of EGFR. In a preferred embodiment, the oligonucleotides comprise at least one phosphorothioate linkage. In other preferred embodiments, the oligonucleotides may comprise at least one 5-methyl cytosine, 2'-O-alkyl or 2'-fluoro modification. Pharmaceutical compositions comprising the oligonucleotides of the invention and a pharmaceutically acceptable carrier are also provided. Farther provided are methods of modulating the expression of a human epidermal growth factor receptor in cells or tissues comprising contacting said cells or tissues with the oligonucleotide of the invention. These methods may be performed in vitro, in vivo or ex vivo. Methods of treating an animal having a hyperproliferative disease or condition by administering a therapeutically effective amount of an oligonucleotide of the invention for a time sufficient to ameliorate said hyperproliferative disease or condition are provided. The hyperproliferative disease or condition may be cancer, and in preferred embodiments the cancer is lung cancer, ovarian cancer, colon cancer or prostate cancer.

DETAILED DESCRIPTION OF THE INVENTION

The present invention employs oligonucleotides for use in inhibiting the function of nucleic acid molecules encoding EGFR, ultimately modulating the amount of EGFR produced. This is accomplished by providing oligonucleotides complementary to mRNA which specifically hybridize with mRNA or DNA encoding EGFR. Such hybridization with mRNA interferes with the normal role of mRNA and causes a modulation of its function. The functions of mRNA to be interfered with include all vital functions such as, for example, translocation of the RNA to the site of protein translation, translation of protein from the RNA, splicing of the RNA to yield one or more mRNA species, and catalytic activity which may be engaged in by the RNA. The overall effect of such interference with mRNA function is modulation of the expression of EGFR. In the context of this invention, "modulation" means either an increase (stimulation) or a decrease (inhibition) in the expression of a gene. In the context of the present invention, inhibition is the preferred form of modulation of gene expression.

Oligonucleotides may comprise nucleotide sequences sufficient in identity and number to effect specific hybridization with a particular nucleic acid molecule. Such oligonucleotides are commonly described as "complementary to mRNA." Oligonucleotides may also be directed to nucleotide sequences within the genome. oligonucleotides are commonly used as research reagents and diagnostics. For example, oligonucleotides complementary to mRNA, which are able to inhibit gene expression with exquisite specificity, are often used by those of ordinary skill to elucidate the function of particular genes. oligonucleotides complementary to mRNA are also used, for example, to distinguish between functions of various members of a biological pathway. This specific inhibitory effect has, therefore, been harnessed for research use.

The specificity and sensitivity of oligonucleotides is also harnessed by those of skill in the art for therapeutic uses. Oligonucleotides have been employed as therapeutic moieties in the treatment of disease states in animals and man. For example, workers in the field have now identified oligonucleotides complementary to mRNA, triplex oligonucleotides, and other oligonucleotide compositions which are capable of modulating expression of genes implicated in viral, fungal and metabolic diseases. Oligonucleotides complementary to mRNA have been safely administered to humans and numerous clinical trials are presently underway. It is thus established that oligonucleotides can be useful therapeutic modalities that can be configured to be useful in treatment regimes for treatment of cells, tissues and animals, especially humans.

It is preferred to target specific genes for attack by oligonucleotides complementary to mRNA. "Targeting" an oligonucleotide to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding EGFR. The targeting process also includes determination of a site or sites within this gene for the oligonucleotide interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed MRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokayotic genes which have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding EGFR, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an MRNA in the 5' direction from the translation initiation codon, and thus including nucleotides between the 5' cap site and the translation initiation codon of an mRNA or corresponding nucleotides on the gene) and the 3' untranslated region (3'UTR), known in the art to refer to the portion of an MRNA in the 3' direction from the translation termination codon, and thus including nucleotides between the translation termination codon and 3' end of an MRNA or corresponding nucleotides on the gene). mRNA splice sites may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. Such rearrangements or deletions of the EGFR gene resulting in mutant EGFR protein are known to occur in some cancers. Once the target site has been identified, oligonucleotides are chosen which are sufficiently complementary to the target, i.e., hybridize sufficiently well and with sufficient specificity, to give the desired effect.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. A discussion of antisense oligonucleotides and some desirable modifications can be found in De Mesmaeker et al., *Acc. Chem. Res.*, 1995, 28, 366.

Specific examples of some preferred oligonucleotides envisioned for this invention include those containing modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, and in particular —$CH_2$—NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$— and —O—N($CH_3$)—$CH_2$—$CH_2$— backbones, wherein the native phosphodiester backbone is represented as —O—P—O—$CH_2$—). The amide backbones disclosed by De Mesmaeker et al. (Id.) are also preferred. Also preferred are oligonucleotides having morpholino backbone structures, such as those described in Summerton and Weller, U.S. Pat. No. 5,034,506.

In other preferred embodiments, such as the peptide nucleic acid (PNA) backbone, the phosphodiester backbone of the oligonucleotide is replaced with a polyamide backbone, the nucleobases being bound directly or indirectly to the aza nitrogen atoms of the polyamide backbone. Nielsen et al., *Science*, 1991, 254, 1497.

Oligonucleotides may also contain one or more substituted sugar moieties. Preferred oligonucleotides comprise one of the following at the 2' position: OH, SH, $SCH_3$, F, OCN, $OCH_3OCH_3$, $OCH_3O(CH_2)_nCH_3$, $O(CH_2)_nNH_2$ or $O(CH_2)_nCH_3$ where n is from 1 to about 10; $C_1$ to $C_{10}$ lower alkyl, alkoxyalkoxy, substituted lower alkyl, alkaryl or aralkyl; Cl; Br; CN; $CF_3$; $OCF_3$; O—, S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide, and other substituents having similar properties. A preferred modification includes 2'-methoxyethoxy (2'—O—$CH_2CH_2OCH_3$, also known as 2'—O—(2-methoxyethyl)) (Martin et al., *Helv. Chim. Acta*, 1995, 78, 486). Other preferred modifications include 2'-methoxy (2'—O—$CH_3$), 2'-propoxy (2'-$OCH_2CH_2CH_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligonucleotides may also include, additionally or alternatively, nucleobase (often referred to in the art simply as "base") modifications or substitutions. As used herein, t"unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-me pyrimidines, particularly 5-methylcytosine (also referred to as 5-methyl-2'deoxycytosine and often referred to in the art as 5-me-C), 5-hydroxymethylcytosine (HMC), glycosyl HMC and gentobiosyl HMC, as well as synthetic nucleobases, e.g., 2-aminoadenine, 2-thiouracil, 2-thiothymine, 5-bromouracil, 5-hydroxymethyluracil, 8-azaguanine, 7-deazaguanine, $N^6$ (6-aminohexyl)adenine and 2,6-diaminopurine. Kornberg, A., DNA Replication, W. H. Freeman & Co., San Francisco, 1980, pp.75–77 and Gebeyehu et al., *Nuc. Acids Res.*, 1987, 15, 4513. A "universal" base known in the art, e.g., inosine, may be included. 5-me-C substitutions have been shown to increase nucleic acid duplex stability by 0.6–1.2° C. (Sanghvi, Y. S., Crooke, S. T. and Lebleu, B., eds., Antisense Research and Applications, CRC Press, Boca Raton,1993, pp. 276–278) and are presently preferred base substitutions.

Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety (Letsinger et al., *Proc. Natl. Acad. Sci. USA*, 1989, 86, 6553), cholic acid (Manoharan et al., *Bioorg. Med. Chem. Let.*, 1994, 4, 1053), a thioether, e.g., hexyl-S-tritylthiol (Manoharan et al., *Ann. N.Y. Acad. Sci.*, 1992, 660, 306; Manoharan et al., *Bioorg. Med. Chem. Let.*, 1993, 3, 2765), a thiocholesterol (Oberhauser et al., *Nucl. Acids Res.*, 1992, 20, 533), an aliphatic chain, e.g., dodecandiol or undecyl residues (Saison-Behmoaras et al., *EMBO J.*, 1991, 10, 111; Kabanov et al., *FEBS Lett.*, 1990, 259, 327; Svinarchuk et al., *Biochimie*, 1993, 75, 49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651; Shea et al., *Nucl. Acids Res.*, 1990, 18, 3777), a polyamine or a polyethylene glycol chain (Manoharan et al., *Nucleosides & Nucleotides*, 1995, 14, 969), or adamantane acetic acid (Manoharan et al., *Tetrahedron Lett.*, 1995, 36, 3651), a palmityl moiety (Mishra et al., *Biochim. Biophys. Acta*, 1995, 1264, 229), or an octadecylamine or hexylaminocarbonyl-oxycholesterol moiety (Crooke et al., *J. Pharmacol. Exp. Ther.*, 1996, 277, 923), all references being incorporated herein by reference. Oligonucleotides comprising lipophilic moieties, and methods for preparing such oligonucleotides are known in the art, for example, U.S. Pat. No. 5,138,045, U.S. Pat. No. 5,218,105 and U.S. Pat. No. 5,459,255, all of which are incorporated herein by reference.

The oligonucleotides of the invention may be provided as prodrugs, which comprise one or more moieties which are cleaved off, generally in the body, to yield an active oligonucleotide. One example of a prodrug approach is described by Imbach et al. in WO Publication 94/26764, incorporated herein by reference.

It is not necessary for all positions in a given oligonucleotide to be uniformly modified, and in fact more than one of the aforementioned modifications may be incorporated in a single oligonucleotide or even at a single nucleoside within an oligonucleotide. The present invention also includes oligonucleotides which are chimeric oligonucleotides. "Chimeric" oligonucleotides or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

The oligonucleotides in accordance with this invention preferably comprise from about 8 to about 30 nucleotides. It is more preferred that such oligonucleotides comprise from about 12 to 25 nucleotides. As is known in the art, a nucleotide is a base-sugar combination suitably bound to an adjacent nucleotide through a phosphodiester, phosphorothioate or other covalent linkage.

The oligonucleotides used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides such as the phosphorothioates and alkylated derivatives.

The oligonucleotides of the present invention can be utilized as diagnostics, therapeutics and as research reagents and kits. For therapeutics, an animal, preferably a human, suspected of having a disease or disorder which can be treated by modulating the expression of EGFR is treated by administering oligonucleotides in accordance with this invention. The oligonucleotides of the invention can be utilized in pharmaceutical compositions by adding an effective amount of an oligonucleotide to a suitable pharmaceutically acceptable diluent or carrier. Use of the oligonucleotides and methods of the invention may also be useful prophylactically, e.g., to prevent or delay tumor formation.

The oligonucleotides of the present invention can be used as diagnostics for the presence of EGFR-specific nucleic acids in a cell or tissue sample. For example, radiolabeled oligonucleotides can be prepared by $^{32}$p labeling at the 5' end with polynucleotide kinase. Sambrook et al., *Molecular Cloning: A Laboratory Manual*, Cold Spring Harbor Laboratory, 1989, Volume 2, pg. 10.59. Radiolabeled oligonucleotides are then contacted with cell or tissue samples suspected of containing EGFR mRNA (and thus, EGFR), and the samples are washed to remove unbound oligonucleotide. Radioactivity remaining in the sample indicates the presence of bound oligonucleotide, which in turn indicates the presence of nucleic acids complementary to the oligonucleotide, and can be quantitated using a scintillation counter or other routine means. Expression of nucleic acids encoding these proteins is thus detected.

Radiolabeled oligonucleotides of the present invention can also be used to perform autoradiography of tissues to determine the localization, distribution and quantitation of EGFR for research, diagnostic or therapeutic purposes. In such studies, tissue sections are treated with radiolabeled oligonucleotide and washed as described above, then exposed to photographic emulsion according to routine autoradiography procedures. The emulsion, when developed, yields an image of silver grains over the regions expressing an EGFR gene. Quantitation of the silver grains permits detection of the expression of mRNA molecules encoding EGFR proteins and permits targeting of oligonucleotides to these areas.

Analogous assays for fluorescent detection of expression of EGFR can be developed using oligonucleotides of the present invention which are conjugated with fluorescein or other fluorescent tags instead of radiolabeling. Such conjugations are routinely accomplished during solid phase synthesis using fluorescently-labeled amidites or controlled pore glass (CPG) columns. Fluorescein-labeled amidites and CPG are available from, e.g., Glen Research, Sterling VA.

Oligonucleotides of the present invention directed to EGFR can be used in diagnostics, therapeutics, prophylaxis, and as research reagents and kits. Because these oligonucleotides hybridize to nucleic acids encoding EGFR, sandwich and other assays can easily be constructed to exploit this fact. Hybridization of the oligonucleotides of the invention with a nucleic acid encoding an EGFR can be detected by means known in the art. Such means may include conjugation of an enzyme to the oligonucleotide, radiolabelling of the oligonucleotide or any other suitable detection systems. Kits for detecting the presence or absence of EGFR may also be prepared.

In the context of this invention, "hybridization" means hydrogen bonding, which may be Watson-Crick, Hoogsteen or reversed Hoogsteen hydrogen bonding, between complementary nucleotides. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that an oligonucleotide need not be 100% complementary. to its target DNA sequence to be specifically hybridizable. An oligonucleotide is specifically hybridizable when binding of the oligonucleotide to the target DNA or RNA molecule interferes with the normal function of the target DNA or RNA to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment, or in the case of in vitro assays, under conditions in which the assays are performed.

The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, pulmonary administration, e.g., by inhalation or insufflation, or intrathecal or intraventricular administration. For oral administration, it has been found that oligonucleotides with at least one 2'-substituted ribonucleotide are particularly useful because of their absorption and distribution characteristics.

U.S. Pat. No. 5,591,721 issued to Agrawal et al. Oligonucleotides with at least one 2'-methoxyethyl modification are believed to be particularly useful for oral administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral, intrathecal or intraventricular administration may include sterile aqueous solutions which may also contain buffers, diluents and other suitable additives.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 μg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 μg to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Oligonucleotide Synthesis

Unmodified oligodeoxynucleotides were synthesized on an automated DNA synthesizer (Applied Biosystems model 380B) using standard phosphoramidite chemistry with oxidation by iodine. β-cyanoethyldiisopropyl-phosphoramidites were purchased from Applied Biosystems (Foster City, Calif.). For phosphorothioate oligonucleotides, the standard oxidation bottle was replaced by a 0.2 M solution of $^3$H-1,2-benzodithiole-3-one 1,1-dioxide in acetonitrile for the stepwise thiation of the phosphite linkages. The thiation cycle wait step was increased to 68 seconds and was followed by the capping step.

2'-methoxy oligonucleotides were synthesized using 2'-methoxy β-cyanoethyldiisopropyl-phosphoramidites (Chemgenes, Needham Mass.) and the standard cycle for unmodified oligonucleotides, except the wait step after pulse delivery of tetrazole and base was increased to 360 seconds. Other 2'-alkoxy oligonucleotides were synthesized by a modification of this method, using appropriate 2'-modified amidites such as those available from Glen Research, Inc., Sterling, Va.

2'-fluoro oligonucleotides were synthesized as described in Kawasaki et al., *J. Med. Chem.* 1993, 36, 831. Briefly, the protected nucleoside $N^6$-benzoyl-2'-deoxy-2'-fluoroadenosine was synthesized utilizing commercially available 9β-D-arabinofuranosyladenine as starting material and by modifying literature procedures whereby the 2'-α-fluoro atom is introduced by a $S_N2$-displacement of a 2'-β-O-trifyl group. Thus $N^6$-benzoyl-9β-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

The synthesis of 2'-deoxy-2'-fluoroguanosine was accomplished using tetraisopropyldisiloxanyl (TPDS) protected 9-β-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

Synthesis of 2'-deoxy-2'-fluorouridine was accomplished by the modification of a literature procedure in which 2,2'-anhydro-1-β-D-arabinofuranosyluracil was treated with 70% hydrogen fluoride-pyridine. Standard procedures were used to obtain the 5'-DMT and 5'-DMT-3' phosphoramidites.

2'-deoxy-2'-fluorocytidine was synthesized via amination of 2'-deoxy-2'-fluorouridine, followed by selective protection to give $N^4$-benzoyl-2'-deoxy-2'-fluorocytidine. Standard procedures were used to obtain the 5'-DMT and 5'-DMT-3' phosphoramidites.

2'-(2-methoxyethyl)-modified amidites are synthesized according to Martin, *Helv. Chim. Acta*, 1995, 78, 486. For ease of synthesis, the last nucleotide was a deoxynucleotide. 2'-O-CH$_2$CH$_2$OCH$_3$-cytosines may be 5-methyl cytosines.

5-methyl-2'-deoxycytidine (5-me-C) containing oligonucleotides were synthesized according to published methods (Sanghvi et al., *Nuc. Acids Res.*, 1993, 21, 3197) using commercially available phosphoramidites (Glen Research, Sterling Va. or ChemGenes, Needham Mass.).

Oligonucleotides having methylene(methylimino) backbones are synthesized according to U.S. Pat. No. 5,378,825, which is coassigned to the assignee of the present invention and is incorporated herein in its entirety. Other nitrogen-containing backbones are synthesized according to WO 92/20823 which is also coassigned to the assignee of the present invention and incorporated herein in its entirety.

Oligonucleotides having amide backbones are synthesized according to De Mesmaeker et al., *Acc. Chem. Res.*, 1995, 28, 366. The amide moiety is readily accessible by simple and well-known synthetic methods and is compatible with the conditions required for solid phase synthesis of oligonucleotides.

Oligonucleotides with morpholino backbones are synthesized according to U.S. Pat. No. 5,034,506 (Summerton and Weller).

Peptide-nucleic acid (PNA) oligomers are synthesized according to P. E. Nielsen et al., *Science* 1991, 254, 1497).

After cleavage from the controlled pore glass column (Applied Biosystems) and deblocking in concentrated ammonium hydroxide at 55° C. for 18 hours, the oligonucleotides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}$P nuclear magnetic resonance spectroscopy, and for some studies oligonucleotides were purified by HPLC, as described by Chiang et al., *J. Biol. Chem.*, 1991, 266, 18162. Results obtained with HPLC-purified material were similar to those obtained with non-HPLC purified material.

Example 2

Cell Culture:

Human SKOV3 ovarian carcinoma cells were obtained from the American Type Culture Collection. They were grown in McCoy's 5A medium containing NaHCO$_3$, 10% fetal bovine serum and antibiotics and routinely passaged. A549 human lung carcinoma cells were routinely passaged in DMEM medium supplemented with 10% fetal bovine serum.

Example 3

Treatment of Cells with Oligonucleotide:

SKOV3 and A549 cells were grown in T-75 flasks until 65–75% confluent. The cells were washed once with serum-free OPTI-MEM® medium (Life Technologies, Inc., Grand Island, N.Y.) and 5 ml of the serum-free OPTI-MEM® containing 15 μg/ml of LIPOFECTIN® reagent (a 1:1 liposome formulation of the cationic lipid DOTMA and DOPE, Life Technologies, Inc.) was added. At that time, 300 nM of oligonucleotide was added and swirled vigorously. After a 4–5 hour incubation at 37° C., the solution was removed and fresh maintenance medium containing 10% fetal bovine serum was added. The cells were again incubated overnight at 37° in 5% CO$_2$, after which the cells were assayed for EGFR MRNA expression or cell growth.

Example 4

Measurement of EGFR mRNA by Northern Blot Analysis:

Total mRNA was extracted from the cells. For SKOV3 cells, cells were washed twice with PBS and 1–2 ml of RNAZOL B® (Tel-Test, Inc., Friendswood Tex.) was added. An incubation at 4° C. for 5–30 minutes was done and the cells were scraped into an Eppendorf tube. This solution was frozen at −80° C. for 20 minutes, thawed and chloroform (200 µl/ml) was added. The solution was centrifuged at 12,000×g for 15 minutes at 4° C. and the aqueous layer was transferred to a clean Eppendorf tube. An equal volume of isopropanol was added and incubated at room temperature for 15 minutes. Another centrifugation at 12,000×g for 15 minutes at 4° C. was done. The pellet was washed with 500 µl of 75% ethanol and centrifuged at 7500×g for 5 minutes at 4° C. As much of the supernatant as possible was removed and the pellet was resuspended in 30 µl of double distilled water. For A549 cells, total mRNA was extracted using a guanidinium/cesium chloride extraction protocol as described by Dean et al., *J. Biol. Chem.*, 1994, 269, 16416. Ten µg of this mRNA was resolved on a 1.0% agarose gel containing 3.0% formaldehyde and transferred to a nylon membrane. The membrane was hybridized with a one-way PCR-generated human EGFR probe radiolabeled with [α-$^{32}$P]-dCTP (Dupont NEN Research Products, Boston Mass.) generated with the GeneAMP PCR Reagent Kit (Perkin Elmer, Foster City Calif.), a T7 primer and a human EGFR transcription template (Ambion, Austin Tex.). The membrane was exposed to autoradiography film at −80° C. and the MRNA bands quantitated using a densitometer (Molecular Dynamics). Blots were stripped of radioactivity by boiling and then reprobed with a $^{32}$P-labeled control probe which hybridized either to G3PDH (Clontech Laboratories, Inc., Palo Alto Calif.) or β-actin (Ambion, Austin Tex.).

Example 5
Metabolic Labeling and Immunoprecipitation of EGFR:

SKOV3 cells were treated with the indicated oligonucleotides in serum-free, methionine-free OPTI-MEM® medium for 2.5 hours. The medium was then replaced with methionine-free OPTI-MEM® containing $^{35}$S-methionine (100 µCi/ml) and 2% dialyzed fetal bovine serum for 10 hours. Cell extracts were prepared as described by Kumar et al., *Proc. Natl. Acad. Sci. USA*, 1992, 89, 6599. Aliquots containing equal amounts of trichloroacetic acid-precipitable counts per minute were subjected to immunoprecipitation with anti-EGFR monoclonal antibody 528/rabbit anti-mouse IgG/protein A-Sepharose conjugate. Kumar et al., *Proc. Natl. Acad. Sci. USA*, 1992, 89, 6599 and Korutla et al., *Carcinogenesis*, 1995, 16, 1741. Lysates containing equal amounts of protein were also resolved on a 10% SDS-polyacrylamide gel and stained with Coomassie blue.

Example 6
Analysis of Antisense Effects on the Growth of SKOV3 Cells:

SKOV3 cells were treated with oligonucleotides ISIS 10563, 12876 and 12877 or the scrambled control oligonucleotide ISIS 12139 as described in Example 3, or left untreated. Cells were then either allowed to grow for 3 additional days in maintenance medium with 10% fetal bovine serum or they were treated again with oligonucleotide at 24 and 48 hours, for 4–5 hours each time. Cells were counted on a Coulter counter at 24, 48 and 72 hours.

Example 7
Synthesis of Particular Oligonucleotides:

The following are examples in which methods and compositions of the present invention have been used effectively. The present invention is not limited to these targets or these compositions. In accordance with the present invention, a series of oligonucleotides complementary to mRNA were designed to target different regions of the human EGFR mRNA, using published sequences (Ullrich et al., *Nature*, 1984, 309, 418; GenBank Accession Number X00588 and Kraus et al., *Proc. Natl. Acad. Sci. USA*, 1989, 86, 9193; GenBank Accession Number M29366). Several analogs of these sequences were also designed. The oligonucleotides are shown in Table 1. Target sites are indicated by source reference (Ullrich or Kraus) and nucleotide numbers, as given in the GenBank listing, to which the oligonucleotide binds.

TABLE 1

| ISIS # | SEQUENCE (5' to 3') | MODIFICATION | TARGET SITE | SEQ ID NO: |
|---|---|---|---|---|
| 10560 | GAGGCGTTCTCCTTTCTCCA | | coding region, Ullrich 2966–2985 | 1 |
| 12878 | GAGGCGTTCTCCT<u>UUCUCCA</u> | 2'-O-propyl | " | 2 |
| 12879 | GAGGCGTTCTCCT<u>UUCUCCA</u> | 2'-fluoro | " | 2 |
| 10561 | TGTCGGCCCCACAGGCTCGG | | coding region, Ullrich 1110–1129 | 3 |
| 10562 | CGCCCGGAGCACTGCTGGGC | | coding region, Ullrich 832–851 | 4 |
| 10563 | CCCCAGCAGCTCCCATTGGG | | coding region, Ullrich 769–788 | 5 |
| 12875 | <u>CCCCAGCAGCTCCCAUUGGG</u> | 2'-fluoro | " | 6 |
| 12876 | <u>CCCCAGCAGCTCCC</u>ATTGGG | 5-methyl C | " | 5 |
| 10564 | CCACGTTGCACAGGGCAGGG | | 5' UTR, Ullrich 645–664 | 7 |
| 10565 | CTCGGCTGACATTCCGGCAA | | coding region, Ullrich 1761–1780 | 8 |
| 12877 | CUCGGCTGACATT<u>CCGGCAA</u> | 2'-fluoro | | 9 |
| 12139 | GAGTTCGCGTCCTTTCTCCA | | scrambled control | 7 10 |

All backbones are phosphorothioates. Oligonucletides for which no additional modification is indicated contain only 2'-deoxynucleotides. Oligonucletides for which a modification is indicated are modified at underlined nucleosides.

Example 8
Effect of Oligonucleotides on EGFR mRNA Levels

Some of the oligonucleotides in Table 1 were tested for their ability to inhibit EGFR mRNA expression in A549 human lung carcinoma cells and SKOV3 human ovarian carcinoma cells, both of which overexpress the EGFR. Cultured cells were treated with 300 nM of oligonucleotide in the presence of 15 μg/ml of cationic lipid (LIPOFECTIN®). Total RNA was extracted and quantitated by Northern blot analysis, using PCR-generated EGFR cDNA probes. Bands were quantitated on a densitometer and normalized to control probe bands (G3PDH for the A549 cells and β-actin for the SKOV3 cells). The results are shown in Table 2 as EGFR mRNA inhibition (10 kb band) as percent of untreated control. The scrambled control, ISIS 12139 (SEQ ID NO:10), actually gave a slight increase in EGFR mRNA compared to untreated controls (18% increase in A549 cells, 39% in SKOV3 cells).

TABLE 2

| | % Inhibition | | |
|---|---|---|---|
| ISIS # | A549 | SKOV3 | SEQ ID NO: |
| 12878 | 66 | 22 | 2 |
| 10561 | 75% | 45% | 3 |
| 10563 | 95 | 61 | 5 |
| 12876 | 97 | 66 | 5 |
| 12875 | 77 | 57 | 6 |
| 10565 | 43 | 33 | 8 |
| 12877 | 93 | 61 | 9 |

A reduction in the amount of the 5.6 kb band was also observed after treatment with each of these oligonucleotides.

Three oligonucleotides, ISIS 10563 (SEQ ID NO:5, phosphorothioate deoxyoligonucleotide), ISIS 12876 (SEQ ID NO:5, 5-methyl C) and ISIS 12877 (SEQ ID NO:9, 2'-fluoro) gave the greatest amount of reduction of EGFR mRNA expression in both cell types. These compounds are, therefore, most preferred, and were further assessed for their effects on EGFR protein production and cell growth. ISIS 12875 was slightly less potent but is also highly preferred. ISIS 12878 and ISIS 10561 gave greater than 50% inhibition of EGFR mRNA expression in A549 cells, and are also preferred.

Example 9
Effect of Oligonucleotides on EGFR Protein Synthesis:
ISIS 10563, ISIS 12876 and ISIS 12877 were added to exponentially growing SKOV3 cells. Cells were metabolically labeled with $^{35}$S-methionine and newly synthesized EGFR protein was immunoprecipitated. A 90–98% reduction of EGFR protein production was observed in cells treated with each of these oligonucleotides compared to untreated cells. Cells treated with scrambled control oligonucleotide (ISIS 12139, SEQ ID NO:10) had a 10% reduction in EGFR synthesis. This inhibition is specific to EGFR protein production, as demonstrated by the presence of an identical number of TCA-precipitable counts per minute in oligonucleotide-treated cells and control cells (either untreated or scrambled control-treated). Coomassie blue staining confirmed that proteins other than EGFR were not affected by treatment of cells with antisense oligonucleotides.

Example 10
Effect of Oligonucleotide Treatment on Growth Of SKOV3 Cells:
Cells were treated with oligonucleotides for 4–5 hours and allowed to grow an additional three days in maintenance medium. Cell counts at 24 hours showed a reduction in cell number of 13–24% for antisense-treated cells compared to untreated or scrambled control-treated cells. Cells treated with repeated oligonucleotide doses at 24 and 48 hours showed a sustained inhibition of cell growth of approximately 30% after 72 hours.

What is claimed is:

1. An oligonucleotide 12–25 nucleotides in length comprising a nucleotide sequence complementary to the 5' untranslated region or coding region of a nucleic acid molecule encoding a human epidermal growth factor receptor, wherein said oligonucleotide inhibits the expression of said human epidermal growth factor receptor.

2. The oligonucleotide of claim 1 comprising SEQ ID NO:1, SEQ ID NO:2, SEQ ID NO:3, SEQ ID NO:4, SEQ ID NO:5, SEQ ID NO:6, SEQ ID NO:7, SEQ ID NO:8 or SEQ ID NO:9.

3. The oligonucleotide of claim 1 comprising SEQ ID NO:1, SEQ ID NO:3, SEQ ID NO:5, or SEQ ID NO:8.

4. The oligonucleotide of claim 1 which contains at least one phosphorothioate intersugar linkage.

5. The oligonucleotide of claim 1 consisting of SEQ ID NO:5.

6. The oligonucleotide of claim 5 in which every cytosine residue is a 5-methyl cytosine.

7. The oligonucleotide of claim 1 consisting of SEQ ID NO:8.

8. The oligonucleotide of claim 7 which has at least one 2'-fluoro or 2'-O-alkyl modification.

9. A composition comprising the oligonucleotide of claim 1 and a pharmaceutically acceptable carrier or diluent.

10. A method of modulating the expression of a human epidermal growth factor receptor in cells or tissues in vitro or ex vivo comprising contacting said cells or tissues with the oligonucleotide of claim 1.

11. The method of claim 10 wherein said oligonucleotide comprises a nucleotide sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, and SEQ ID NO:9.

12. An oligonucleotide 12–25 nucleorides in length comprising at least one base modification or 2'-modification and comprising a nucleotide sequence complementary to the 5' untranslated region, or coding region of a nucleic acid molecule encoding a human epidermal growth factor receptor, wherein said oligonucleotide inhibits the expression of said human epidermal growth factor receptor.

13. The oligonucleotide of claim 12 comprising SEQ ID NO:1, SEQ ID NO:2, SEQ ID NO:3, SEQ ID NO:4, SEQ ID NO:5, SEQ ID NO:6, SEQ ID NO:7, SEQ ID NO:8 or SEQ ID NO:9.

14. The oligonucleotide of claim 12 comprising SEQ ID NO:1, SEQ ID NO:3, SEQ ID NO:5, or SEQ ID NO:8.

15. The oligonucleotide of claim 12 which contains at least one phosphorothioate intersugar linkage.

16. The oligonucleotide of claim 12 consisting of SEQ ID NO:5.

17. The oligonucleotide of claim 16 in which every cytosine residue is a 5-methyl cytosine.

18. The oligonucleotide of claim 12 consisting of SEQ ID NO:8.

19. The oligonucleotide of claim 18 which has at least one 2'-fluoro or 2'-O-alkyl modification.

20. A composition comprising the oligonucleotide of claim 12 and a pharmaceutically acceptable carrier or diluent.

21. A method of modulating the expression of a human epidermal growth factor receptor in cells or tissues in vitro or ex vivo comprising contacting said cells or tissues with an oligonucleotide 12–25 nucleotides in length comprising at least one base modification or 2'-modification and comprising a nucleotide sequence complimentary to the 5' untranslated region or coding region of a nucleic acid molecule encoding a human epidermal growth factor receptor.

22. The method of claim 21 wherein said oligonucleotide comprises a nucleotide sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, and SEQ ID NO:9.

23. The method of claim 21 wherein said oligonucleotide comprises a nucleotide sequence selected from the group consisting of SEQ ID NO:1, SEQ ID NO:3, SEQ ID NO:5, or SEQ ID NO:8.

* * * * *